(12) United States Patent
Majumder et al.

(10) Patent No.: US 8,389,787 B1
(45) Date of Patent: Mar. 5, 2013

(54) CONTROL OF 2-PHENYL CONTENT IN ALKYLBENZENES DURING PRODUCTION

(75) Inventors: Debarshi Majumder, Forest Park, IL (US); Stephen W. Sohn, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/426,129

(22) Filed: Mar. 21, 2012

(51) Int. Cl.
*C07C 2/66* (2006.01)
(52) U.S. Cl. ........................................ 585/455; 585/467
(58) Field of Classification Search .................. 585/455, 585/467
See application file for complete search history.

(56) References Cited

U.S. PATENT DOCUMENTS

| | | | |
|---|---|---|---|
| 5,648,579 | A | 7/1997 | Kulprathipanja et al. |
| 6,521,804 | B1 | 2/2003 | Marinangeli et al. |
| 2006/0287562 | A1 | 12/2006 | Guillon et al. |
| 2008/0161619 | A1 | 7/2008 | Riley et al. |
| 2009/0062583 | A1* | 3/2009 | Guillon et al. ................ 585/301 |
| 2009/0299091 | A1 | 12/2009 | Goncalvez De Almeida et al. |

FOREIGN PATENT DOCUMENTS

| | | |
|---|---|---|
| EP | 1568675 A1 | 8/2005 |
| EP | 2233461 A1 | 9/2010 |
| FR | 2854628 A1 | 11/2004 |

OTHER PUBLICATIONS

Berna et al., Evaluation of the Rheological Properties of Sulfonic Acids and Sodium Sulfonates, Journal of Surfactants and Detergents, vol. 3, No. 3, Jul. 2000, pp. 353-359.
Cohen et al., Influence of 2-Phenyl Alkane and Tetralin Content on Solubility and Viscosity of Linear Alkylbenzene Sulfonate, JAOCS, vol. 72, No. 1 1995, pp. 115-122.
Moreno et al., L.A.B. Composition Influence on L.A.S., Tenside Surfactants Detergents 25 (1988) 4, pp. 216-221.

\* cited by examiner

*Primary Examiner* — Thuan D Dang
(74) *Attorney, Agent, or Firm* — Arthur E. Gooding

(57) ABSTRACT

A process is presented for the management and control of the 2-phenyl content in a benzene alkylation process. The process includes the use of multiple reactor beds, with benzene flowing through the reactor beds in a sequential manner. The olefin stream is split to two or more portions, and a separate portion is passed to the first reactor bed and second reactor bed. Control of the ratio of the olefin flow splits controls the 2-phenyl content.

17 Claims, 2 Drawing Sheets

CONTROL OF 2-PHENYL CONTENT IN ALKYLBENZENES DURING PRODUCTION

FIELD OF THE INVENTION

The present invention is directed to the process of generating a detergent grade intermediate product of alkylbenzenes. The process is for controlling and maintaining the 2-phenyl content in the alkylbenzene product.

BACKGROUND OF THE INVENTION

Linear alkylbenzenes (LAB) are compounds that have significant commercial importance. Linear alkylbenzene sulfonate (LAS) compounds made by sulfonation of linear alkylbenzene are used in the manufacture of detergents and other products. Because linear alkylbenzenes are more easily biodegradable than branched alkylbenzenes, linear alkylbenzenes have essentially replaced branched alkylbenzenes in detergents and other products. In particular, linear alkylbenzenes with long alkyl chains, such as chains having about 10 to about 14 carbons, are commonly used. However, linear alkylbenzenes with longer chains and with shorter chains also are commercially important.

Linear alkylbenzenes often are made by alkylation of benzene with olefins. Positional isomers, such as 2-phenyl, 3-phenyl, 4-phenyl, 5-phenyl, and the like, result from this alkylation of benzene with long chain olefins. The distribution of the phenyl along the alkyl chain produces different products.

Historically, linear alkylbenzenes are manufactured commercially using classic Friedel-Crafts condensation employing catalysts such as aluminum chloride, or by using strong acid catalysts such as hydrogen fluoride, for example, to alkylate benzene with olefins. In 1995, a solid bed alkylation process, the Detal™ process, using a solid non-corrosive acid catalyst was introduced. While such methods produce high conversions, the selectivity to the 2-phenyl isomer typically is about 30 percent or less. Linear alkylbenzenes with a high percentage of the 2-phenyl isomer are highly desired because such compounds when sulfonated have long tails that provide enhanced solubility and detergent properties.

The 2-phenyl isomer content of the product is process dependent. Solid alkylation catalysts, such as those used in the Detal™ process, produce products with 2-phenyl isomer content between 25 and 30 percent. HF-catalyzed processes typically yield a 2-phenyl isomer content less than 20 percent, and $AlCl_3$ typically between 30 and 33 percent. The properties of linear alkylbenzenes and linear alkylbenzene sulfonate produced from these three processes have been disclosed by Berna and coworkers in the following publications. Journal of Surfactants and Detergents, Vol. 3, No. 2 (July 2000) pages 353 through 359, JAOCS, Vol. 72, No. 1 (1995) pages 115 through 122, and Tenside Surfactants Detergents 25 (1988) 4, pages 216 through 221.

Zeolite catalysts also have been used to obtain linear alkylbenzenes by alkylation of benzene with olefins. The 2-phenyl isomer content of linear alkylbenzenes obtained using such catalysts depends on the zeolite selected and can vary from about 20 percent to 90 percent. However, some zeolitic catalysts are quickly deactivated, and very high concentration of 2-phenyl isomer in linear alkylbenzene yields a linear alkylbenzene sulfonate that dissolves poorly in water. Most zeolites, with the exception of FAU, produce linear alkylbenzene with 2-phenyl isomer content higher than existing commercial processes.

The differences in linear alkylbenzene compositions produce different linear alkylbenzene sulfonate products. The products differ not only in composition but also in properties and characteristics. Some of the properties that detergent formulators need to consider are solubility, viscosity, detergency performance, foaming power, foam stability, hard water stability, and biodegradability. A number of these properties are dependent on the isomeric composition of the linear alkylbenzene sulfonate.

Thus, there exists a need for a method for controlling 2-phenyl isomer content of linear alkylbenzenes obtained by alkylating benzene with olefins.

SUMMARY OF THE INVENTION

The present invention provides for improved control over the 2-phenyl content in an alkylbenzene product stream. The process provides on-the-fly control by controlling the distribution of olefin feeds to reactor beds. The process includes passing a benzene stream to a first reactor bed in a system with a plurality of reactor beds comprising two or more reactor beds. The benzene flows through the reactor beds in a sequential manner. An olefin feedstream is split into at least two olefin streams, creating at least a first olefin stream and a second olefin stream. The sum of the olefin streams comprises the total olefin flow, and is equal to the olefin feedstream. The first olefin stream is passed to the first reactor bed, where the benzene and olefin react over a catalyst to form a first reactor bed effluent stream comprising benzene and alkylbenzene. The first reactor bed effluent and the second olefin stream is passed to a second reactor bed, where the benzene and olefin react over a catalyst to form a second reactor bed effluent stream, comprising an alkylbenzene product. The ratio of the second olefin stream to the total olefin flow is controlled to generate a specified 2-phenyl content in the alkylbenzene product. By monitoring the 2-phenyl content in the product, the ratio of the second olefin stream to the total olefin stream is adjusted to maintain a desired specification.

Other objects, advantages and applications of the present invention will become apparent to those skilled in the art from the following detailed description and drawings.

DETAILED DESCRIPTION OF THE INVENTION

Figure 1:
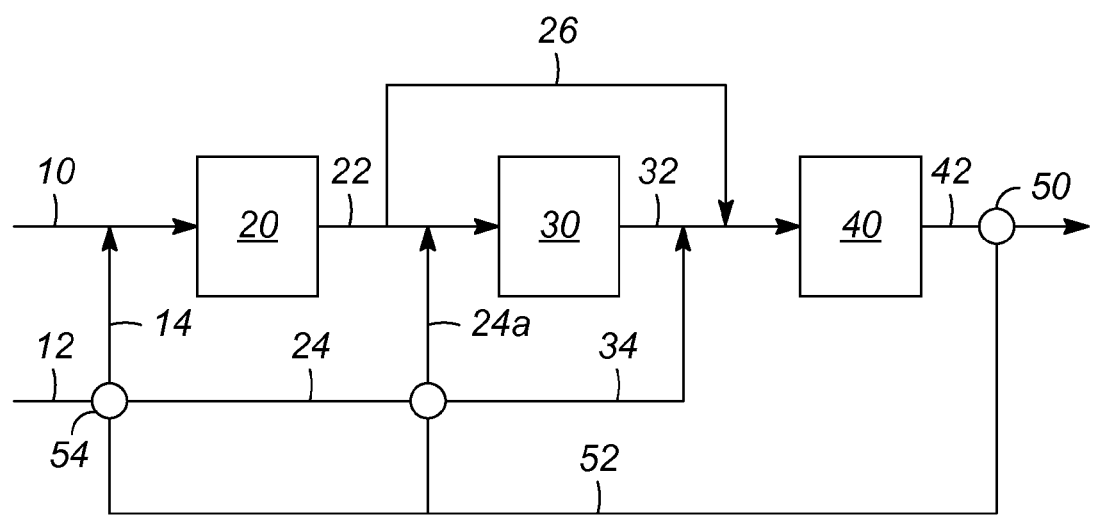
FIG. 1 is a diagram of the process control.

Alkylbenzenes, also known as phenyl alkanes, are important for many different products. When the alkyl group has 9 to 20 carbon atoms, among the common usages is the predominant use in the formation of detergents. Alkylbenzenes are an intermediate product used to form alkylbenzene sulformates, which are surfactants that form the basis of many detergents. The alkylbenzene sulfonates are known to exhibit different physical properties based upon the position of the aromatic group on the alkyl chain. In the production of alkylbenzene sulfonates, the intermediate product alkylbenzenes are generated with the intention to produce a product with the benzene group near the end of the alkyl group, with the 2-position the desired result. The product stream can be rated by its 2-phenyl content, and alkylbenzene sulfonates having a higher 2-phenyl content have higher solubility and viscosity in an aqueous media. The control of the 2-phenyl content of the intermediate product is therefore advantageous for the downstream processing of the end product alkylbenzene sulfonate specification.

During a production cycle of the alkylbenzenes, there is a gradual deactivation of the catalyst over the duration of the production cycle. The gradual deactivation of the catalyst results in a shift in the 2-phenyl content of the alkylbenzene product as the catalyst deactivates. Controlling the 2-phenyl content is important for increasing the operating run times between regeneration cycles in the alkylation process. Also, controlling the 2-phenyl content through control of the feed distribution between the reactors provides a consistent 2-phenyl content over time.

The present invention provides for control of the benzene alkylation process to maintain the 2-phenyl content of the alkylbenzene product. The process includes passing a benzene stream to a first reactor in a system comprising a plurality of reactor beds. Where the reactor beds are arranged in a series relationship. A single type of catalyst is used for all the reactor beds. An olefin stream is split into at least two olefin streams, creating at least a first olefin stream and a second olefin stream, with the sum of the olefin streams comprising the total olefin flow. The first olefin stream is passed to the first reactor bed to react with the benzene and generate a first reactor bed effluent stream. The first reactor bed effluent stream and the second olefin stream are passed to a second reactor bed, thereby generating a second reactor bed effluent stream. The second reactor bed effluent stream is monitored to determine the 2-phenyl content of the alkylbenzene product. The ratio of the second olefin stream to the total olefin flow is adjusted to maintain a specified 2-phenyl content in the alkylbenzene product. A single type of catalyst provides benefits in terms of controlling the process over several reactor beds, without having to account for differences if one were to use different catalysts in the different beds. With multi-catalyst systems, more complications arise from the differing rates of deactivation, regeneration, and long term stability. In addition should two or more catalysts be mixed, there can be segregation during operation in a fluidized bed system, through the movement of catalyst particles.

The second reactor bed effluent stream is passed to a fractionation system to separate benzene and residual olefins from the second bed effluent stream to generate the alkylbenzene product stream. The benzene can be recycled to the reactor beds, along with any residual olefins. The normal operation of the reactor beds is to consume the olefins, thereby minimizing the residual olefins in the effluent stream.

The process can further comprises a third reactor bed operated at benzene alkylation conditions, where the second reactor bed effluent stream is passed to the third reactor bed and generates a third reactor bed effluent stream comprising the alkylbenzene product. In one option, the feed olefin stream can be split into three olefin streams, where a first olefin stream is passed to the first reactor bed, a second olefin stream is passed to the second reactor bed, and a third olefin stream is passed to the third reactor bed. Benzene is combined with the first olefin stream and passed to the first reactor bed to generate a first bed effluent stream. The first bed effluent stream is combined with the second olefin stream and passed to the second reactor bed to generate a second reactor bed effluent stream. The second reactor bed effluent stream is combined with the third olefin stream and passed to the third reactor bed to generate a third reactor bed effluent stream.

An alternative embodiment for a three reactor bed system includes splitting the first reactor bed effluent into a first portion and a second portion. The first portion is combined with the second olefin stream and passed to the second reactor bed to generate a second reactor bed effluent stream. The second portion is combined with the second reactor bed effluent stream and the third olefin stream and passed to the third reactor bed to generate a third reactor bed effluent stream comprising the alkylbenzene product.

The process can include more reactor beds, with the olefin feed split into two or more olefin streams. The effluent stream leaving the last reactor bed in the series is passed to a product recovery unit. The product recovery unit can be a fractionation column to separate benzene from the effluent to generate a benzene stream for recycle and an alkylbenzene product stream.

The reactor beds in the process include a benzene alkylation catalyst for alkylating benzene with an olefin, where the olefins in the olefin feedstream have from 9 to 20 carbon atoms. Detergent range alkylbenzenes are often formed with a narrower range of carbon atoms in the alkyl group, and the olefins will typically have from 9 to 16 carbon atoms.

The process is illustrated in FIG. 1. A benzene stream 10 is fed to a first reactor bed 20. An olefin stream 12 is split into two streams, a first olefin stream 14 and a second olefin stream 24. The first olefin stream 14 is passed to the first reactor 20, and with the benzene generates a first reactor effluent stream 22. The first reactor effluent stream 22 is passed with the second olefin stream 24 to a second reactor bed 30 to generate a second reactor bed effluent stream 32. In the simplest system of two beds, the second reactor bed effluent stream 32 is monitored by a device 50 to determine the 2-phenyl content of the alkylbenzene. A feedback control sends an appropriate signal 52 to control the ratio of the second olefin stream 24 to the olefin feedstream 12.

With a three reactor system, the second reactor effluent stream 32 is passed to the third reactor 40 to generate a fourth reactor effluent stream 42, with the effluent stream 42 having the alkylbenzene product. The alkylbenzene in the effluent stream 42 is monitored for its 2-phenyl content by the monitoring device 50 and the flow split is controlled by a valve 54 for splitting the olefin feed 12. Other options include further splitting the olefin feed into three parts. One method includes splitting the second olefin stream 24 into two portions, 24a and 34. The first portion 24a is directed to the second reactor bed 30, and the second portion 34 is directed to the third reactor bed 40.

Another option in the three reactor bed system includes splitting the first reactor bed effluent stream 22, with a first portion directed to the second reactor bed 30, and a second portion 26 directed to the third reactor bed 40.

In another embodiment, the monitoring device 50 can be positioned after the product recovery unit (not shown), where the alkylbenzene product is monitored for its 2-phenyl content. The ratio of the second olefin stream 24 to the olefin feed stream 12 is adjusted to maintain a substantially constant 2-phenyl content in the alkylbenzene product stream.

The process is intended to cover many combinations with two or more reactor beds, where the control can also be extended to adjust olefin flows to the third or subsequent reactor beds. While there are potentially an unlimited number of combinations as the number of beds is increased, the practical number of beds is from two to five, with the olefin feed split between two to three of the reactor beds.

The alkylation process with benzene and olefins in the 9 to 20 carbon range is preferably carried out as a liquid phase reaction. The alkylation conditions include a reaction temperature between 80° C. and 200° C., most usually at a temperature not exceeding 175° C., e.g., 100° C. to 160° C. Typically, as the catalyst ages, the temperature of the alkylation is increased to maintain desired activity. The alkylation is an exothermic reaction and thus in a substantially adiabatic reactor, the effluent is at a higher temperature than that of the feed. A substantially adiabatic reactor is one where the increase in temperature of the effluent over that of the feed accounts for at least about 75 percent of heat generated by the reactions in the reaction zone. The preferred aromatic compound is benzene, and the temperature can be maintained within a given range by providing an excess of the aromatic compound. Additional designs can include heat exchangers, or coolers, between reactor beds.

To maintain the reactants in the liquid phase, the reactor is operated at a pressure between 1300 and 7000 kPa, with a preferred operating pressure between 2000 and 4000 kPa. The process conditions include an overall benzene to olefin molar feed ratio, for a ratio of benzene to total olefin feed, between 3 and 20. A preferred ratio is between 4 and 12.

It is important that an alkylbenzene process unit be designed at a fixed overall benzene supply flow rate to the benzene alkylation reactor. This allows for a fixed sizing of the upstream benzene column that supplies the benzene. The use of a multi-bed reactor configuration allows for flexibility in the relative flow rates of benzene and olefin to the reactor by varying locally the amount of olefin to each reactor bed in the multi-bed reactor system. This enables rapid and easy control of the 2-phenyl content by changing the olefin flow rates to the different reactor beds.

Figure 2:
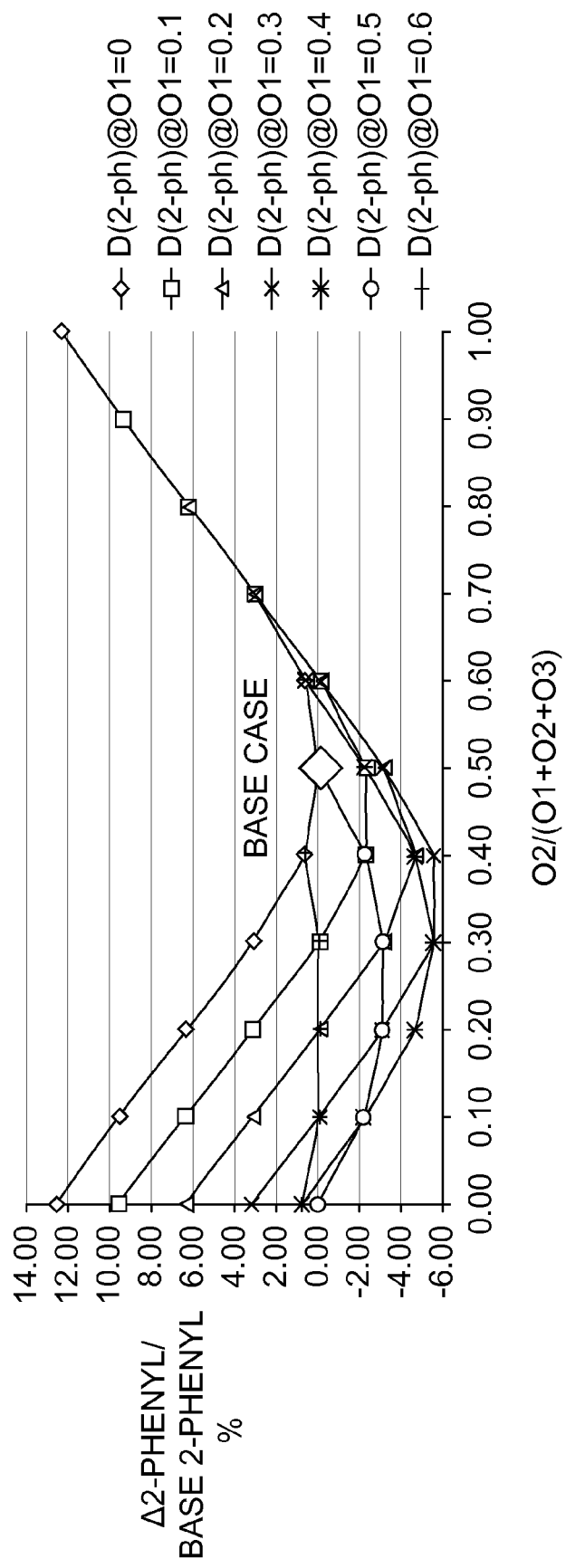
FIG. 2 is a diagram showing the response to the change in 2-phenyl content with the change in olefin feed splits to a multi-reactor system.

A specific example of a three bed reactor system shows the results from pilot plant experiments in FIG. 2. The overall benzene to olefin flow molar ratio was 10 to 1, and a reference case used a 50:50 split of the olefin feed to the first and second reactor beds with a zero olefin stream to the third reactor bed. By varying the olefin split to the first and second reactor beds, the 2-phenyl content was shown to vary between −6% and +13% from the reference case. The shifting of the split, or the relative amount of olefin to the second reactor, can adjust the 2-phenyl content about the base case 2-phenyl content. This demonstrates the ability to shift the 2-phenyl content with respect to a target value by shifting the olefin stream splits. This also allows for control over time as the catalyst slowly deactivates. In this series of runs, the three beds are interchangeable in that interchanging the flows will have no effect on the 2-phenyl content of the product stream.

While this process is amenable to any catalyst useable in linear alkylbenzene (LAB) production, it is known that skeletal isomerization of linear olefins occurs in the production of LAB over solid acid catalysts. In 1965, in an article titled "Hydroisomerization of Normal Olefins Under Alkylation Conditions" showed that skeletal isomerization was favored by high acid concentrations and high temperatures (Peterson, A. H., Phillips, B. L., and Kelly, J. T., *I&EC*, 4, No. 4, 261-265, 1965). Also, as shown in U.S. Pat. No. 4,301,317 to Young, Table 2 compares the amount of linear phenyldodecane produced by alkylation of 1-dodecene with benzene over eight different zeolites. All of the zeolites exhibited skeletal isomerization. Inhibiting skeletal isomerization is an important challenge to be addressed, if one is to produce highly linear detergent range alkylbenzenes. It is further worth noting that Beta zeolite, which is commonly used in the production of ethylbenzene and cumene is unsuitable for detergent range LAB production due to its tendency to skeletally isomerizes the linear olefins prior to their alkylation. Because ethylene and propylene only have one isomer, both the double bond and skeletal isomerization of the catalyst are moot and for this reason one cannot predict that a process or catalyst for ethylbenzene or cumene production will necessarily extend to LAB. Therefore, while not intending this process to be limited to newer catalyst, the use of newer catalysts are amenable to this process.

One such catalyst comprises a mixture of two types of zeolitic materials, where the zeolites are mixed and produced to have two zeolites within a single catalyst pellet. With the new catalysts, the first zeolite is also characterized by its acidity, wherein the acidity is characterized by having less than 70% of $NH_3$ desorption off the zeolite at temperatures greater than 400° C. The $NH_3$-TPD experimental procedure comprises: calibration of the $NH_3$-TPD system with 5 injections of 0.2 cc pulses of $NH_3$ at 2 minute intervals into a flow of UHP grade helium at 40 cc/minute. The data collected from the Thermal Conductivity Detector is integrated and used to calibrate the detector response to a known quantity of $NH_3$. An equilibrated sample, for moisture content is weighed at approximately 250 mg and placed in the reactor. The sample is pretreated in a flow of 20% $O_2$/He UHP grade at a rate of 100 cc/minute and with a temperature ramp of 10° C./minute up to a maximum temperature of 650° C. The sample is held at this temperature for one hour, then purged with UHP grade helium for 15 minutes and cooled to the saturation temperature. The pretreatment is for removal of water and residual contaminants. The sample is saturated with anhydrous $NH_3$ at 150° C. using multiple pulses of $NH_3$ injected into He flowing at 40 cc/min. The minimum quantity of $NH_3$ used to saturate the sample is 50 cc. The excess ammonia is purged from the sample in flowing (40 cc/min) UHP grade helium for ~8 hours. The $NH_3$ is desorbed from the sample in a flow (40 cc/min) of UHP grade helium with a temperature ramp of 10° C./minute to a final temperature of about 605° C. All gases have been purified using appropriate gas purifiers. The $NH_3$ desorbed is detected with a Thermal Conductivity Detector. The detector response is converted to moles of $NH_3$ using the detector response obtained at the beginning of the experiment. The integrated results are reported by integration of the temperature range of interest and reported as mmoles $NH_3$/g sample. An example of the first zeolite is UZM-8.

The second zeolite having a silica to alumina molar ratio less than 8, and includes a rare earth element incorporated into the zeolitic framework in an amount greater than 16.5 wt %. The first zeolite component is in an amount between 10 and 90% by weight of the catalyst, and the second zeolite component is in an amount between 10 and 90% by weight. The zeolites are intermingled into single catalyst particles. An example of the second zeolite is a rare earth substituted X zeolite, Y zeolite, or a zeolite having an EMT/FAU intergrowth. The incorporation of rare earth exchanged ions in a low ratio zeolite reduces the acidity due to an increase in the number of framework alumina at low ratios, and also reduces geometric space in the supercage. The reduced acidity and reduced space significantly suppresses the isomerization and cracking pathways, while the leaving the primary alkylation reaction unaffected. This decreases the undesired side reactions that reduce the amount and quality of the LAB product. This is contrary to what one would expect, as it has been found that incorporating or leaving some alkali or alkaline earth cations in the catalyst significantly improves the catalyst performance. This is especially true with respect to the performance around the linearity of the alkylbenzene, and the retention of linearity as the operating temperatures are increased. Normally, the alkali or alkaline earth cations are removed because without the rare earth exchange, the alkali or alkaline earth cations are detrimental to the catalyst life and regenerability.

Therefore, improvements in product quality can be achieved through innovative control of the flow of reactants, and by controlling the relative flows to different reactors, the life of the process before regeneration of the catalyst can be increased. While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for controlling the 2-phenyl content of an alkylbenzene product stream comprising:
passing a benzene stream into a first reactor in a plurality of reactor beds in a series arrangement, wherein the plurality of reactors comprises two or more reactors and each reactor bed is operated at benzene alkylation reaction conditions, wherein a single catalyst type is used for all of the reactor beds, wherein the catalyst comprises a first zeolite comprising UZM-8 and a second zeolite comprising a rare earth substituted X or Y zeolite intermingled into single catalyst particles;
splitting a feed olefin stream to at least two olefin streams, creating at least a first olefin stream and a second olefin stream, where the sum of the olefin streams comprises the total olefin flow, wherein the olefin comprises olefins having from 9 to 20 carbon atoms;
passing the first olefin stream to the first reactor bed, thereby generating a first reactor bed effluent stream;
passing the first reactor bed effluent stream and the second olefin stream to a second reactor bed thereby generating a second reactor bed effluent stream, comprising an alkylbenzene product; and
controlling the ratio of second olefin stream to the total olefin flow to generate a specified 2-phenyl content of the alkylbenzene product.

2. The process of claim 1 further comprising passing the second reactor bed effluent stream to a third reactor bed operated at benzene alkylation reaction conditions to generate the alkylbenzene product.

3. The process of claim 1 further comprising:
splitting the feed olefin stream into three olefin streams, where there are three reactor beds;
passing the first olefin stream to the first reactor bed, to generate a first reactor bed effluent stream;
passing the second olefin stream and the first reactor bed effluent to the second reactor bed, to generate a second reactor bed effluent stream; and
passing the third olefin stream and the second reactor bed effluent to the third reactor bed, to generate the alkylbenzene product stream.

4. The process of claim 3 further comprising:
splitting the first reactor bed effluent into a first portion of the first reactor bed effluent and a second portion of the first reactor bed effluent;
passing the first portion of the first reactor bed effluent and the second olefin stream to the second reactor bed, to generate a second reactor bed effluent;
passing the second portion of the first reactor bed effluent, the second reactor bed effluent, and the third olefin stream to the third reactor bed, to generate the alkylbenzene product stream.

5. The process of claim 1 wherein the reaction conditions include a liquid phase reaction process with a temperature between 80 C and 200 C.

6. The process of claim 1 wherein the reaction conditions include a liquid phase reaction process with a pressure between 1300 kPa and 7000 kPa.

7. The process of claim 1 wherein the benzene to the total olefin flow molar ratio is between 3 and 20.

8. The process of claim 6 wherein the benzene to the total olefin flow molar ratio is between 4 and 12.

9. The process of claim 1 further comprising:
monitoring the 2-phenyl content of the alkylbenzene product stream; and
adjusting the splitting of the feed olefin stream between the first and second olefin streams.

10. A process for controlling the 2-phenyl content of an alkylbenzene product stream comprising:
passing a benzene stream to a first reactor in a plurality of reactor beds in a series arrangement, wherein the plurality of reactors comprises three reactors and each reactor bed is operated at benzene alkylation reaction conditions, wherein the same catalyst type is used in each reactor bed, wherein the catalyst comprises a first zeolite comprising UZM-8 and a second zeolite comprising a rare earth substituted X or Y zeolite intermingled into single catalyst particles;
splitting a feed olefin stream into three olefin streams, creating a first olefin stream, a second olefin stream, and a third olefin stream, where the sum of the olefin streams comprises the total olefin flow, wherein the olefins comprise olefins having from 9 to 20 carbon atoms;
passing the first olefin stream to the first reactor bed, thereby generating a first reactor bed effluent stream;
passing the first reactor bed effluent stream and the second olefin stream to a second reactor bed thereby generating a second reactor bed effluent stream;
passing the second reactor bed effluent stream and the third olefin stream to a third reactor bed thereby generating a third reactor bed effluent stream;
controlling the ratio of second olefin stream to the total olefin flow to generate a specified 2-phenyl content of the alkylbenzene product stream; and
monitoring the 2-phenyl content of the alkylbenzene product stream.

11. The process of claim 10 wherein the reaction conditions include a liquid phase reaction process with a temperature between 80 C and 200 C.

12. The process of claim 10 wherein the reaction conditions include a liquid phase reaction process with a pressure between 1300 kPa and 7000 kPa.

13. The process of claim 10 wherein the benzene to the total olefin flow molar ratio is between 3 and 20.

14. The process of claim 13 wherein the benzene to the total olefin flow molar ratio is between 4 and 12.

15. The process of claim 10 further comprising adjusting the splitting of the feed olefin stream between the first, second and third olefin streams.

16. The process of claim 10 wherein the first reactor bed effluent is divided into two portions, and wherein a first portion is passed to the second reactor bed, and a second portion is passed to the third reactor bed.

17. The process of claim 10 wherein the alkylation reactor beds include a benzene alkylation catalyst for alkylating benzene with an olefin having 9 to 16 carbons.

* * * * *